US011278215B2

(12) United States Patent
Demas et al.

(10) Patent No.: US 11,278,215 B2
(45) Date of Patent: Mar. 22, 2022

(54) RHINOMETRIC SENSING AND GAS DETECTION

(71) Applicant: Massachusetts Institute of Technology, Cambridge, MA (US)

(72) Inventors: Nickolas Peter Demas, Watertown, MA (US); Ian W. Hunter, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/174,922

(22) Filed: Feb. 12, 2021

(65) Prior Publication Data

US 2021/0161428 A1    Jun. 3, 2021

Related U.S. Application Data

(63) Continuation of application No. PCT/US2020/046630, filed on Aug. 17, 2020.
(Continued)

(51) Int. Cl.
*G01N 33/497* (2006.01)
*A61B 5/091* (2006.01)
(Continued)

(52) U.S. Cl.
CPC ............ *A61B 5/091* (2013.01); *A01K 29/005* (2013.01); *A61B 5/087* (2013.01); *A61B 5/0833* (2013.01);
(Continued)

(58) Field of Classification Search
CPC ...................... G01N 33/497; G01N 2033/4975
(Continued)

(56) References Cited

U.S. PATENT DOCUMENTS 3,398,365 A    8/1968   Var
3,622,958 A   11/1971   Tucker et al.
(Continued)

FOREIGN PATENT DOCUMENTS

DE    102008014300 A1    9/2009
EP       0572581 B1     1/1997
(Continued)

OTHER PUBLICATIONS

Clement et al., "Consensus report on acoustic rhinometry and rhinomanometry." Rhinology 43.3 (2005): 169-179.
(Continued)

*Primary Examiner* — John Fitzgerald
*Assistant Examiner* — Rodney T Frank
(74) *Attorney, Agent, or Firm* — Smith Baluch LLP

(57) ABSTRACT

An acoustic system can track gas emissions by exploiting the nostril-accessible nasal pathways of an animal. Actuators and microphones used in the apparatus can be similar to those currently found in cell phones, which in turn make the acoustic apparatus small and rugged. The nostril geometry can be mapped using sound waves, similar to the mapping done by an acoustic rhinometer. Where acoustic rhinometers assume a constant speed of sound to measure changes in geometry, acoustic approaches as disclosed herein can assume constant geometry to measure changes in the speed of sound. Approaches disclosed here are particularly useful with any gas, such as (for example) methane, hydrogen, helium, etc. that has a speed of sound higher than other typical gaseous components of exhaled air, such as nitrogen, carbon-dioxide, oxygen, etc.

20 Claims, 11 Drawing Sheets

Related U.S. Application Data

(60) Provisional application No. 62/887,042, filed on Aug. 15, 2019.

(51) Int. Cl.
*A01K 29/00* (2006.01)
*A61B 5/083* (2006.01)
*A61B 5/087* (2006.01)
*A61B 7/00* (2006.01)
*G10L 25/66* (2013.01)

(52) U.S. Cl.
CPC ............ *A61B 5/0836* (2013.01); *A61B 7/003* (2013.01); *G01N 33/497* (2013.01); *G10L 25/66* (2013.01); *A61B 2503/40* (2013.01); *A61B 2562/029* (2013.01); *A61B 2562/0271* (2013.01); *G01N 2033/4975* (2013.01); *Y02P 60/50* (2015.11)

(58) Field of Classification Search
USPC .......................................................... 73/23.3
See application file for complete search history.

(56) References Cited

U.S. PATENT DOCUMENTS

| | | |
|---|---|---|
| 4,119,950 A | 10/1978 | Redding |
| 4,326,416 A | 4/1982 | Fredberg |
| 4,976,148 A | 12/1990 | Migliori et al. |
| 5,035,144 A | 7/1991 | Aussel |
| 5,062,296 A | 11/1991 | Migliori |
| 5,211,052 A | 5/1993 | Shakkottai et al. |
| 5,265,618 A | 11/1993 | Zimmerman |
| 5,316,002 A | 5/1994 | Jackson et al. |
| 5,386,714 A | 2/1995 | Dames |
| 5,581,014 A | 12/1996 | Douglas |
| 5,767,408 A | 6/1998 | Lindgren et al. |
| 5,882,314 A | 3/1999 | Fredberg et al. |
| 5,902,237 A | 5/1999 | Glass |
| 6,481,288 B1 | 11/2002 | Humphrey et al. |
| 6,491,641 B1 | 12/2002 | Rasmussen |
| 6,644,119 B1 | 11/2003 | Sinha |
| 8,424,527 B1 | 4/2013 | Kayyali et al. |
| 9,164,081 B2 * | 10/2015 | Van Der Tol ........ G01N 33/497 |
| 2005/0143937 A1 | 6/2005 | Morrow et al. |
| 2005/0154301 A1 | 7/2005 | Shahar et al. |
| 2006/0100666 A1 | 5/2006 | Wilkinson et al. |
| 2007/0161918 A1 | 7/2007 | Ganshorn |
| 2008/0196715 A1 | 8/2008 | Yamamori |
| 2008/0243056 A1 | 10/2008 | Hillis et al. |
| 2009/0288606 A1 | 11/2009 | Zimmerman |
| 2015/0059442 A1 | 3/2015 | Liljenberg et al. |
| 2016/0041286 A1 | 2/2016 | Sinha et al. |
| 2017/0003176 A1 | 1/2017 | Le et al. |
| 2018/0011058 A1 | 1/2018 | Willing |
| 2018/0266996 A1 | 9/2018 | Fokow et al. |

FOREIGN PATENT DOCUMENTS

| | | |
|---|---|---|
| EP | 1205748 A1 | 5/2002 |
| EP | 1353173 A2 | 10/2003 |
| EP | 1441222 A3 | 7/2010 |
| FR | 2134909 | 12/1972 |
| WO | 9203724 A1 | 3/1992 |
| WO | 2013179202 A2 | 12/2013 |

OTHER PUBLICATIONS

Czaja, "Acoustic measurement of subglottic stenosis." Annals of Otology, Rhinology & Laryngology 105.7 (1996): 504-509.
Fisher, "Acoustic rhinometry." Clinical Otolaryngology & Allied Sciences 22.4 (1997): 307-317.
Hammond et al., "Methane emissions from cattle: Estimates from short-term measurements using a GreenFeed system compared with measurements obtained using respiration chambers or sulphur hexafluoride tracer." Animal Feed Science and Technology 203 (2015): 41-52. 37 pages.
Hilberg et al., "Acoustic reflections during rhinometry: spatial resolution and sound loss" Journal of Applied Physiology 84.3 (1998): 1030-1039.
Hilberg et al., "Acoustic rhinometry: evaluation of nasal cavity geometry by acoustic reflection." Journal of applied physiology 66.1 (1989): 295-303.
International Search Report and Written Opinion in International Patent Application No. PCT/US2020/046630 dated Feb. 3, 2021, 17 pages.
Jackson et al., "Airway geometry by analysis of acoustic pulse response measurements." Journal of Applied Physiology 43.3 (1977): 523-536.
Jackson et al., "Comparison of direct and acoustical area measurements in physical models of human central airways." Journal of Applied Physiology 48.5 (1980): 896-902.
Landa et al., "Confirming nasal airway dimensions observed on panoramic and posterior-anterior cephalometric radiographs using an acoustic rhinometer." European Archives of Paediatric Dentistry 11.3 (2010): 115-121.
Mechanics of Breathing: Pathophysiology, Diagnosis and Treatment (Aliverti et al., eds) Springer 2002. 380 pages.
Roithmann et al., "Acoustic rhinometry in the evaluation of nasal obstruction." The Laryngoscope 105.3 (1995): 275-281.
Straszek, "Acoustic Rhinometry (Ar): an alternative method to image nasal airway geometry." Acoustical Imaging. Springer, Dordrecht, 2007. 127-135.
Ware et al., "Continuous and discrete inverse-scattering problems in a stratified elastic medium. I. Plane waves at normal incidence." The journal of the Acoustical Society of America 45.4 (1969): 911-921.
Avnery et al., "Global crop yield reductions due to surface ozone exposure: 2. Year 2030 potential crop production losses and economic damage under two scenarios of O3 pollution." Atmospheric Environment 45.13 (2011): 2297-2309.
Cristofanelli et al., "Background ozone in the southern Europe and Mediterranean area: influence of the transport processes." Environmental Pollution 157.5 (2009): 1399-1406.
Dain et al., "Acoustic attenuation in three-component gas mixtures—Theory." The Journal of the Acoustical Society of America 109.5 (2001): 1955-1964.
Dewey et al., "Acoustic amplifier for detection of atmospheric pollutants." Applied Physics Letters 23.11 (1973): 633-635.
Dewey, "Opto-acoustic spectroscopy." Optical Engineering 13.6 (1974): 136483. 6 pages.
Ejakov et al., "Acoustic attenuation in gas mixtures with nitrogen: experimental data and calculations." The Journal of the Acoustical Society of America 113.4 (2003): 1871-1879.
Electrochemical Oxygen Sensor. CO2 Meter 2016. Accessed at https://web.archive.org/web/20161117073842/http://www.co2meter.com/collections/co2-sensors/products/electrochemical-oxygen-sensor on Apr. 7, 2021. 2 pages.
Electrochemical Sensors. SGX SensorTech. Accessed at https://www.sgxsensortech.com/products-services/industrial-safety/electrochemical-sensors/ on Apr. 7, 2021. 2 pages.
Exhaust gas. Wikipedia Last edited Mar. 1, 2021. Accessed at https://en.wikipedia.org/wiki/Exhaust_gas on Apr. 7, 2021. 11 pages.
Felzer et al., "Impacts of ozone on trees and crops." Comptes Rendus Geoscience 339.11-12 (2007): 784-798.
Fiscus et al., "Crop responses to ozone: uptake, modes of action, carbon assimilation and partitioning." Plant, Cell & Environment 28.8 (2005): 997-1011.
Frigo et al., "The design and implementation of FFTW3." Proceedings of the IEEE 93.2 (2005): 216-231.
Geostationary Coastal and Air Pollution Events (Geo-Cape). NASA Last Updated Dec. 6, 2016. Accessed at https://web.archive.org/web/20170513052807/https://eospso.nasa.gov/missions/geostationary-coastal-and-air-pollution-events on Apr. 7, 2021. 1 page.
Hanwei Eletronics Co., Ltd. Accessed at http://www.hwsensor.com/ on Apr. 7, 2021. 2 pages.

(56) References Cited

OTHER PUBLICATIONS

Heagle, "Ozone and crop yield." Annual review of phytopathology 27.1 (1989): 397-423.
Helmig et al., "Highly elevated atmospheric levels of volatile organic compounds in the Uintah Basin, Utah." Environmental science & technology 48.9 (2014): 4707-4715.
Honeywell Searchpoint Optima Plus Gas Detector. Instrumart. Accessed at https://www.instrumart.com/products/43104/honeywell-searchpoint-optima-plus-gas-detector on Apr. 7, 2021. 6 pages.
Hu et al., "Acoustic absorption spectral peak location for gas detection." Sensors and Actuators B: Chemical 203 (2014): 1-8.
Hunter et al., "Estimation of the conduction velocity of muscle action potentials using phase and impulse response function techniques." Medical and Biological Engineering and Computing 25.2 (1987): 121-126.
Hunter, System Identification Via FFT. Technical report, Massachusetts Institute of Technology, 2010. 7 pages.
Integrated Sensors and Software For Real-Time Air Quality Monitoring. Aeroqual Limited. Accessed at www.aeroqual.com on Apr. 7, 2021. 5 pages.
International Search Report and Written Opinion in International Patent Application No. PCT/US2019/061913 dated Mar. 11, 2020, 15 pages.
Keefe et al., "Wave propagation in strongly curved ducts." The Journal of the Acoustical Society of America 74.1 (1983): 320-332.
Landau, "Theory of sound dispersion" and English Machine Translation. Physikalische zeitschrift der Sowjetunion 10 (1936): 34-43. 24 pages.
Long et al., "Global food insecurity. Treatment of major food crops with elevated carbon dioxide or ozone under large-scale fully open-air conditions suggests recent models may have overestimated future yields." Philosophical Transactions of the Royal Society B: Biological Sciences 360.1463 (2005): 2011-2020.
Maynard, "Resonant ultrasound spectroscopy." Physics Today 49.1 (1996): 26-31.
Metal Oxide Sensors. SGX SensorTech. Accessed at https://www.sgxsensortech.com/products-services/industrial-safety/metal-oxide-sensors/ on Apr. 7, 2021. 1 page.
MiCS Application Note 4 Using MiCS Sensors for Alcohol Detection. e2v technologies Jun. 2009. Accessed at https://sgx.cdistore.com/datasheets/e2v/AN4-Using-MiCS-Sensors-for-Alcohol-Detection1.pdf. 8 pages.
Morse, Acoustical Society of America, and American Institute of Physics. Vibration and sound. vol. 468. New York McGraw-Hill, 1948. 493 pages.
Operating principle. Figaro Engineering Inc. 2018. Accessed at https://www.figaro.co.jp/en/technicalinfo/principle/mos-type.html on Apr. 7, 2021. 3 pages.
Patel, Hasmukh S., and Richard G. Hoft. "Generalized techniques of harmonic elimination and voltage control in thyristor inverters: part II—voltage control techniques." IEEE Transactions on Industry Applications 5 (1974): 666-673.
Petculescu et al., "A prototype acoustic gas sensor based on attenuation." The Journal of the Acoustical Society of America 120.4 (2006): 1779-1782.
Petculescu et al., "Fine-tuning molecular acoustic models: sensitivity of the predicted attenuation to the Lennard-Jones parameters." The Journal of the Acoustical Society of America 117.1 (2005): 175-184.
Petculescu et al., "Synthesizing primary molecular relaxation processes in excitable gases using a two-frequency reconstructive algorithm." Physical review letters 94.23 (2005): 238301. 4 pages.
Photo Ionization Detector. Accessed at http://www.cpeo.org/techtree/ttdescript/photion.htm on Apr. 7, 2021. 2 pages.
Romain et al., "Long term stability of metal oxide-based gas sensors for e-nose environmental applications: An overview." Sensors and Actuators B: Chemical 146.2 (2010): 502-506.
Schwartz et al., "Calculation of vibrational relaxation times in gases." The Journal of Chemical Physics 20.10 (1952): 1591-1599.
Sensors: Oxygen Sensors. CO2Meter.com. Accessed at https://www.co2meter.com/collections/oxygen-sensors on Apr. 7, 2021 8 pages.
Shields, "Sound absorption in the halogen gases." The Journal of the Acoustical Society of America 32.2 (1960): 180-185.
Simon, "Apparatus and techniques for the plane wave analysis of acoustic filters." (1969). 210 pages.
Smith, Osha Releases Guidance for Calibration for Portable Gas Monitors. EHS Today May 16, 2004. Accessed at https://www.ehstoday.com/archive/article/21905140/osha-releases-guidance-for-calibration-for-portable-gas-monitors. 9 pages.
Spec Sensors. Accessed at www.spec-sensors.com on Apr. 7, 2021. 2 pages.
SprintIR®-W 100% CO2 Sensor. CO2Meter.com. Accessed at https://www.co2meter.com/products/sprintir-100-percent-co2-sensor on Apr. 7, 2021. 4 pages.
SSS-903 Gas Detector. ESP Safety Inc. Mar. 2015. Accessed at https://web.archive.org/web/20190121105847/http://www.espsafetyinc.com/esp/cms/userfiles/files/SSS-903_R08.pdf. 2 pages.
State-of-the-art gas sensors. Chapter 3. Apr. 2006. Accessed at https://sundoc.bibliothek.uni-halle.de/diss-online/06/06H053/t4.pdf. 7 pages.
Tanczos, "Calculation of vibrational relaxation times of the chloromethanes." The Journal of Chemical Physics 25.3 (1956): 439-447.
Tashian, Successful Leak Detection Using Ultrasonics. Superior Signal Aug. 2008. Accessed at https://superiorsignal.com/resources/useful-articles/104-successful-leak-detection-using-ultrasonics on Apr. 7, 2021. 7 pages.
TGS 6810-D00. Figaro USA, Inc. Oct. 2014. Accessed at https://web.archive.org/web/20170711234304/http://www.figarosensor.com/products/docs/TGS%206810D00(1014).pdf on Apr. 7, 2021. 2 pages.
Tie et al., "Megacity impacts on regional ozone formation: observations and WRF-Chem modeling for the MIRAGE-Shanghai field campaign." Atmospheric Chemistry and Physics 13.11 (2013): 5655-5669.
US EPA. Understanding Global Warming Potentials, 2019. Accessed at https://www.epa.gov/ghgemissions/understanding-global-warming-potentials. 4 pages.
Vaisala Oyj. Humidity Conversion Formulas. Technical report, Vaisala Oyj, 2013. Accessed at https://www.vaisala.com/sites/default/files/documents/ Humidity_Conversion_Formulas_B210973EN-F.pdf. 17 pages.
Welch, "The use of fast Fourier transform for the estimation of power spectra: a method based on time averaging over short, modified periodograms." IEEE Transactions on audio and electroacoustics 15.2 (1967): 70-73.
Weston, "The theory of the propagation of plane sound waves in tubes." Proceedings of the Physical Society. Section B 66.8 (1953): 695. 16 pages.
Zhu et al., An Algorithm for Carbon Monoxide Concentration. In International Conference on Wavelet Analysis and Pattern Recognition, pp. 332-337, 2007. 6 pages.

* cited by examiner

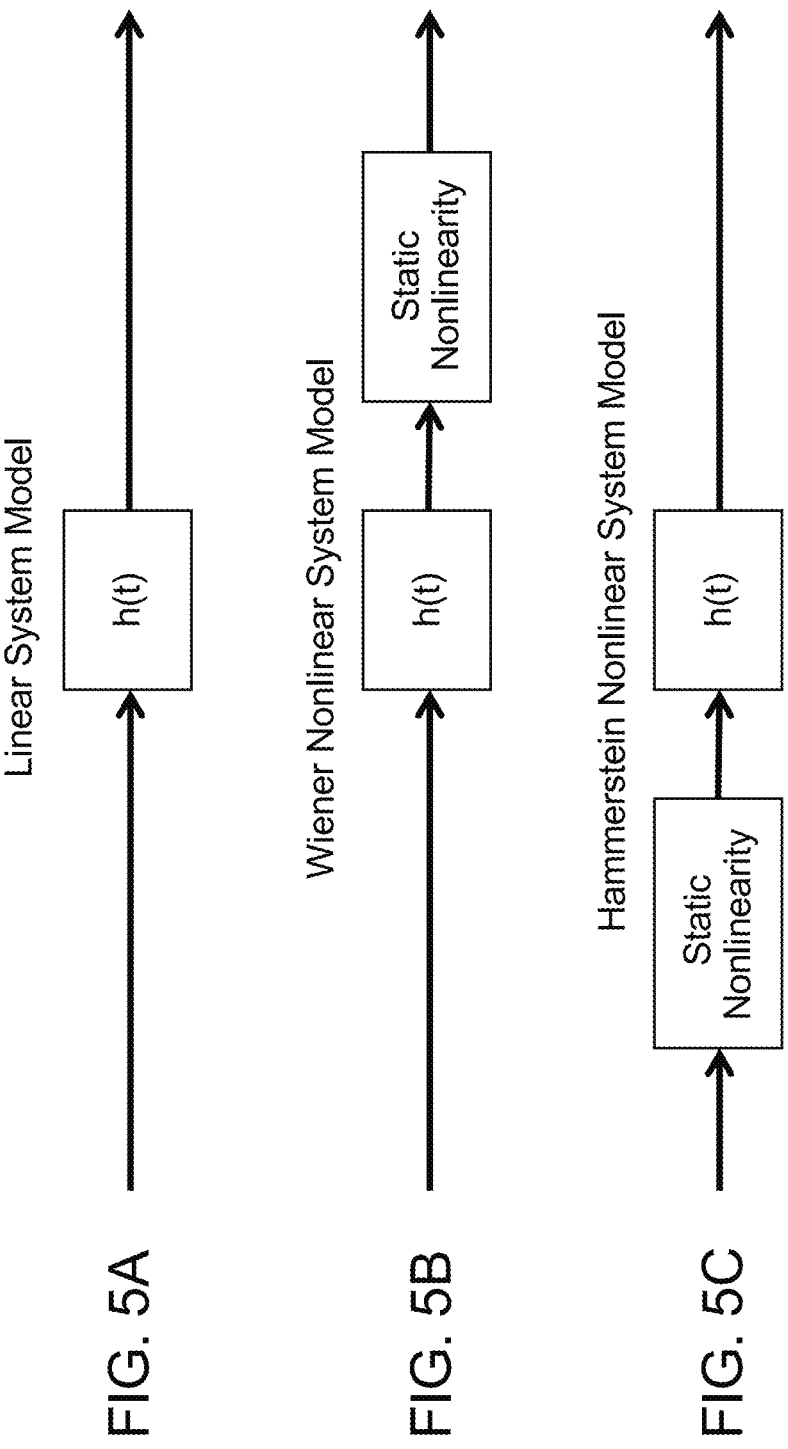

RHINOMETRIC SENSING AND GAS DETECTION

CROSS-REFERENCE TO RELATED APPLICATIONS

This application is a bypass continuation of PCT Application No. PCT/US2020/046630, filed Aug. 17, 2020, which claims priority to U.S. Provisional Application No. 62/887,042 filed Aug. 15, 2019, titled "RHINOMETRIC SENSING AND GAS DETECTION", each of which is incorporated herein by reference.

BACKGROUND

There are over 1.5 billion cattle worldwide, and these animals are a major source of methane. The U.S. Environmental Protection Agency estimates that a quarter of methane emissions due to human activity can be attributed to livestock. Methane, a potent greenhouse gas, has a global warming potential that can be over 20 times worse than carbon dioxide.

In response to these concerns, 15 U.S. states have passed laws that restrict methane emissions. These laws aim to regulate emissions by requiring local agencies to report methane sources and amounts. A key challenge for implementing these laws is how to accurately quantify methane emissions from livestock.

Measuring methane from livestock is difficult for a few reasons. First, over 95% of methane gas emitted from cattle is released from the mouth and nostrils. As a result, sensors should be strategically located to accurately measure gas released by livestock. Second, there is strong demand for tracking methane emission at the individual animal level. For example, studies have indicated that certain additives for cattle feedstock reduces methane emissions. While promising, present global production of these additives cannot meet the needs of all cattle. Given the considerable variation in gas produced between animals over time, the limited supply of effective additive means that farmers have to allocate them efficiently to the largest producers of methane gas at any given time. This can make it desirable to monitor methane gas emissions continuously for each animal in real-time, which is challenging.

Currently, very few farms track methane emissions of individual livestock. Some experimental efforts have used air samples collected by planes to estimate emission levels roughly. Other efforts use a breathalyzer-type instrument that takes measurements when the animal is being fed, but such devices do not allow for continuous measurements, and can be expensive to install. Other efforts use chemical sensors that can be non-selective and suffer from slow response times. Sensors that burn organic gases for detection of specific combustion products need a combustion chamber. Mass spectrometry and gas chromatography are too large and expensive for monitoring individual cows. While surface acoustic wave devices can have a smaller profile, they use selective adsorptive layers that need replacement when they saturate. Other, conventional acoustic attenuation or sound velocity sensors are also too bulky for practical use.

SUMMARY

The present technology and approaches are useful for continuous monitoring of methane emissions from individual, ruminant animals such as cattle.

A method of estimating a concentration of methane emissions from a ruminant animal includes coupling an acoustic actuator to a nasal passageway of the ruminant animal. The method also includes applying an actuation signal to the acoustic actuator to generate and deliver a first acoustic signal into the nasal passageway, such that the nasal passageway reflects the first acoustic signal as a second acoustic signal. The method further includes collectively detecting the first acoustic signal and the second acoustic signal as a third acoustic signal. The method also includes isolating, based on the first acoustic signal, the second acoustic signal from the third acoustic signal and estimating a sound speed through the nasal passageway based on the second acoustic signal. The method further includes estimating methane concentration in the nasal passageway based on the estimated sound speed.

A system for measurement of methane emissions includes an acoustic actuator to generate a first acoustic signal, and a propagation tube, having a proximal end in acoustic communication with the acoustic actuator, to guide the first acoustic signal to a distal end of the propagation tube. The system further includes a delivery tube, coupled to the distal end of the propagation tube, to deliver the first acoustic signal to a nasal passageway of a ruminant animal and to receive a second acoustic signal reflected by the nasal passageway. The system also includes a first microphone, in acoustic communication with a first point on the propagation tube, to detect at least one of the first acoustic signal or the second acoustic signal, and a second microphone, in acoustic communication with a second point on the propagation tube between the first point and the distal end of the propagation tube, to detect a superposition of the first acoustic signal and the second acoustic signal. The system also includes a processor, coupled to the first microphone and the second microphone, to isolate, based on the detected first acoustic signal, the second acoustic signal from the superposition of the first acoustic signal and the second acoustic signal and estimate a sound speed associated with the nasal passageway based on the second acoustic signal. The processor also estimate a sound speed associated with the nasal passageway based on the second acoustic signal.

A method of estimating a concentration of methane emissions from a ruminant animal includes coupling an acoustic actuator to a nasal passageway of the ruminant animal, and applying an actuation signal to the acoustic actuator to generate and deliver a first acoustic signal into the nasal passageway, such that the nasal passageway reflects the first acoustic signal as a second acoustic signal. The method further includes determining an impulse response of the nasal passageway based on the second acoustic signal and estimating a sound speed associated with the nasal passageway based on the impulse response, based on a baseline impulse response of the nasal passageway, the baseline impulse response associated with an absence of methane in the nasal passageway, the baseline impulse response based on an assumption of fixed geometry of the nasal passageway. The method further includes estimating a methane concentration in the nasal passageway based on the sound speed.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may

BRIEF DESCRIPTION OF THE DRAWINGS

FIG. 5A illustrates a linear system model suitable for estimating methane emissions from acoustic signals captured using an acoustic system.

FIG. 5B illustrates a Weiner nonlinear system model suitable for estimating methane emissions from acoustic signals captured using an acoustic system.

FIG. 5C illustrates a Hammerstein nonlinear system model suitable for estimating methane emissions from acoustic signals captured using an acoustic system.

Figure 1:
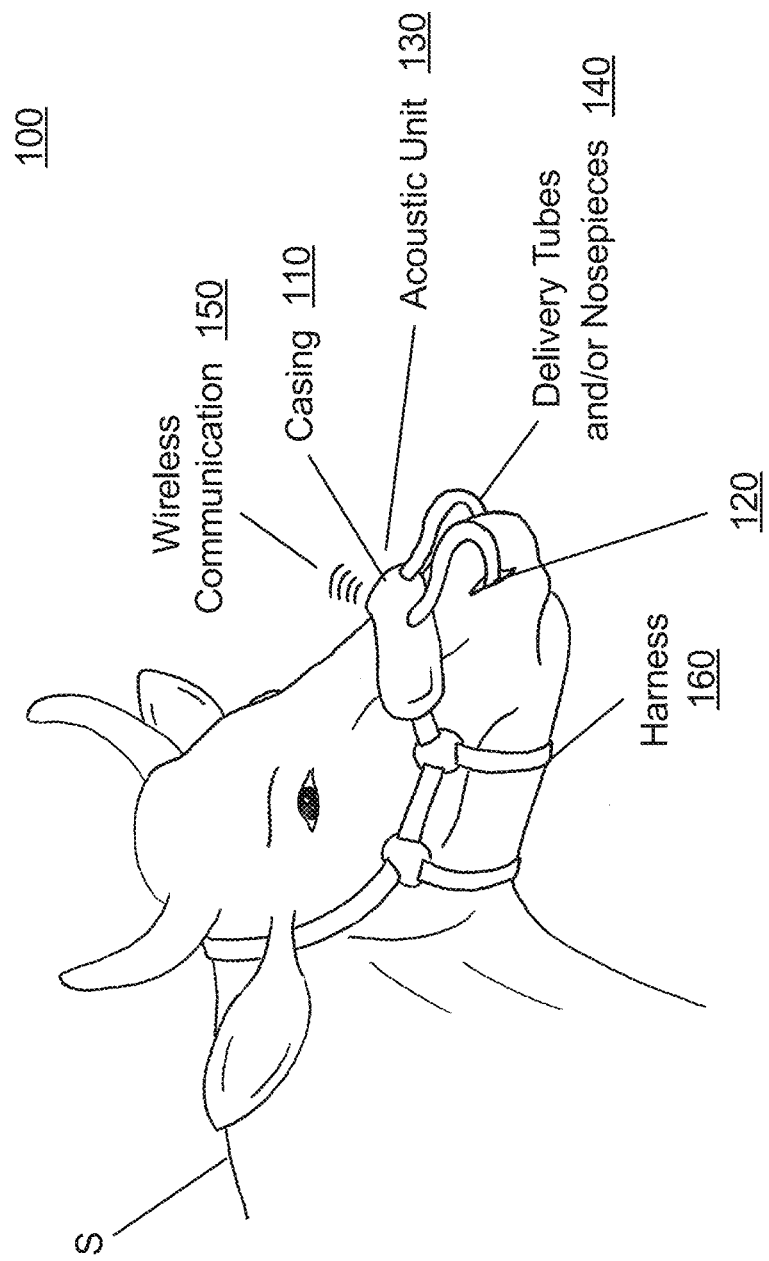
FIG. 1 illustrates an example acoustic system mounted on a subject ruminant animal.

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Aspects disclosed herein are directed to performing real-time gas (e.g., methane) emissions sensing in the respiratory tracts of subjects (e.g., cattle) at the individual level while providing benefits of a small footprint, durability, and the potential for continuous monitoring.

Example acoustic sensing approaches to quantifying methane emissions from cattle are disclosed herein, though such approaches are extendible to quantifying gas emissions from the nasal passages of any suitable subject. Here, an acoustic signal/sound is emitted or injected into the respiratory tract (e.g., including the nasal and throat passages) of the animal, and the reflected sound is measured as a response. Based on this response, the speed of sound in the passages of the subject can be estimated, and the gas makeup in the subject's respiratory tract can be estimated based on the speed of sound and prior knowledge of the types of gases that can be typically encountered. While discussed with respect to the nasal and/or throat passages sometimes, aspects disclosed herein are generally applicable to the entire respiratory tract of the subject, and/or any portion thereof.

FIG. 1 illustrates an example acoustic system 100 in use on a cow/subject S, but is generally applicable to any subject, such as to, for example, any ruminant animal such as goat, sheep, giraffe, deer, gazelle, antelope, cows, bulls that has a rumen portion to its stomach for microbial fermentation of ingested food. The system 100 includes a casing/housing 110 that encloses an acoustic unit 130, which can include or be composed of any material suitable for prolonged outdoor use, that does not hinder wireless communication as described below, and/or the like. For example, the unit 130 can include one or more acoustic generators for generating an acoustic signal, and one or more acoustic sensors for detecting the acoustic response from the nasal passages of the subject, as explained in more detail for FIGS. 2A-2D.

The unit 130 also includes a processor (not shown), which can be any suitable processing device configured to run and/or execute a set of instructions or code associated with the system 100. The processor can be, for example, a general purpose processor, a Field Programmable Gate Array (FPGA), an Application Specific Integrated Circuit (ASIC), a Digital Signal Processor (DSP), and/or the like. The unit 130 can also include a memory/database. The memory/database can encompass, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory/database can store instructions to cause the processor to execute processes and/or functions associated with the system 100.

The unit 130 can also include an interface for wired (no shown) or wireless communication 150 such as, for example, via Bluetooth (including low power Bluetooth), local area network (LAN), a wide area network (WAN), a virtual network, a telecommunications network, direct path/bounce/repeater supported radio communications, direct path optical communications, satellite network, sonic or ultrasonic communications, and/or the Internet, implemented as a wired network and/or a wireless network. All components within the unit 130 can be electrically and/or electronically coupled with each other as required or desired.

The system 100 also includes a set of delivery tubes 140 for delivering the acoustic signal from the unit 130 to the nasal passages of the subject S, and for receiving the reflected response. The delivery tubes 140 can have a substantially constant cross-sectional area, or a gradual and/or continuous change in cross-sectional area, which in turn can minimize/limit the amount of the acoustic signal reflected back from the tubes themselves, and in turn maximize the portion of the acoustic signal that is delivered to the subject S. Generally, since the reflected response will also account for the delivery tubes 140 (i.e., the tubes 140, for purposes of acoustic analysis, will form a part of the measured respiratory tract of the subject S), the geometry of the delivery tubes 140 (including any bending of the tubes as may be necessary or desired for insertion and/or fit), which can be detected and characterized with a rhinometric scan, can provide a measurable, consistent geometric feature which can be accounted for when changes in sound speed and/or gas composition in the respiratory tract of the subject S can be determined. To that end, the delivery tubes 140 can be composed of any suitable material capable of maintaining near constant geometry over an extended period of time. The cross-sectional area of the delivery tubes 140 in some cases can be less than the cross-sectional area of the nostril(s), which can permit the subject S to respire through its nostrils even with the tubes inserted.

The tubes 140 can be directly inserted into the nasal passages, or be coupled to nose pieces (not shown) that in turn are acoustically coupled to the subject S's nasal passages. The nose pieces can include any conformable (e.g., deformable) and/or customized inserts that can form a seal between the tube 140 and its nostril, such that exhaled air from the respiratory tract is substantially directed through the delivery tube. The nose pieces can also be configured to provide a stable mechanical connection of the tube with the nostril, allow for mucus to drain from the nostril without entering and/or filling the delivery tubes 140, position the delivery tubes approximately at the center of the nostril, and/or provide an intermediate geometry that facilitates a smooth, continuous transition of the geometry, cross-sectional area, etc. between the delivery tubes and the nostril. Generally, such optimizations to reduce resistance to respiration-induced flow can encourage the animal to breathe through its nose rather than through its mouth. In some cases, the system 100 can be adapted for use with the mouth of the subject S in whole or in part. For example, the system 100 can be adapted to perturb the air in the throat through the nostril and the gas emission and/or speed of sound can be estimated from the throat/mouth. As another example, the system 100 can be adapted to perturb the air in the throat directly, and the gas emission and/or speed of sound can be estimated from the throat/mouth.

The system 100 further includes a harness 160 for holding the unit 130, and generally the system 100, in place without unduly hindering breathing or movement of the subject S. In this manner, the system 100 can be use for continuous monitoring of the subject S for extended periods of time.

FIGS. 2A-2D illustrate an example acoustic system 200 as a block diagram of the system 100, and illustrates components that can be structurally and/or functionally similar to those described for the system 100. While interchangeably described herein with respect to use with one or two nostrils, it is understood that, for two or more nostrils, each nostrils can be coupled to its own system 200. The system 200 includes a processor 240 (e.g., similar to the processor of the unit 130) coupled to an acoustic actuator 215 (e.g., similar to the acoustic generator of the unit 130) via a digital-to-analog converter (DAC) of a circuit 245 for controlling generation of an acoustic signal by the actuator 215. The DAC converts digital actuation signals from the processor 240 into analog actuation signals suitable for driving the acoustic actuator 215. The acoustic actuator 215 can include, for example, a voice coil, a magneto-striction device, a piezoelectric speaker, an electric spark/arc-based device, a thermal actuator (including shape memory alloy actuators, actuators employing air heating/expansion such as with a laser, and/or the like), etc. The dynamic behavior of the acoustic actuator 215 can be predetermined and/or otherwise determinable, and the actuator should be suitable for prolonged outdoor use, i.e., be robust against humidity, submersion, extreme temperatures, and/or the like.

The system 200 also includes a propagation tube 210, which can be a hollow tube in fluid communication with the nostril(s) N during use. The system 200 also includes a delivery tube 250 (e.g., similar to the tubes 140) coupled to a nose piece 255, which in turn is acoustically coupled to nostril(s) N, such as that of the subject S. During use, the acoustic signal generated by the acoustic actuator 215 is transmitted to the nostrils N via the propagation tube 210, the nose piece 255, and the delivery tube 250, and the acoustic response is collected via the same pathway. As described for the delivery tube 140, the interfaces between these components can be designed to minimize reflection of the acoustic signal back towards the actuator 215, or the reflected response back towards the respiratory tract of the subject S. As described below, the propagation tube can be sized based on a necessary or desired separation between microphones of the system 200, to permit for sufficient resolution between detection of the acoustic signal and the reflected response.

The system 200 also includes a flow sensor 230 disposed at or near one end of the propagation tube 210 to be proximal to the nostrils N, to record flow speed when the subject S exhales. For example, the flow sensor 230 can be coupled to the delivery tube 250, to the propagation tube 210, or both, i.e., the flow sensor 230 can perform the acoustic coupling between the delivery tube 250 and the propagation tube 210. The flow sensor 230 can be additionally employed to determine if the system 200 is properly installed and/or functioning (e.g., if the tubes are inadvertently plugging the subject's nostrils and preventing respiration through the nose). The flow sensor 230 can also be employed to estimate the volume of air flowing through the nostril and the corresponding volume of methane released. The flow sensor 230 can also be employed to determine the direction of flow, and accordingly, whether the subject S is inhaling or exhaling. In some cases, the flow sensor 230 is absent, and the actuator 215, microphones 220, 225 (described below) can be employed to determine any or all of these parameters. Examples of useful flow sensors can include thermal flow sensors (e.g., a hot wire anemometer), a mechanical vane-based flow sensor (e.g., a spirometer), a pressure differential flow sensor, and/or the like.

Figure 2A:
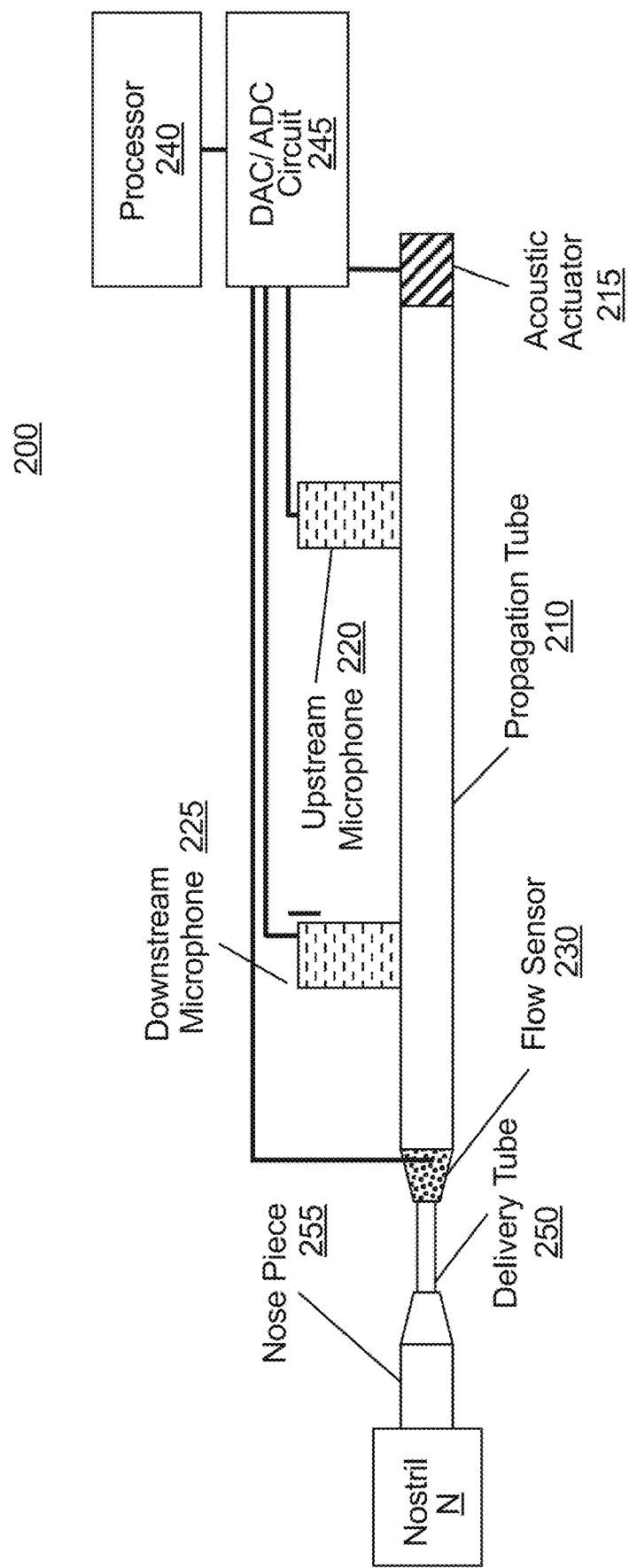
FIG. 2A illustrates components of an example acoustic system.
Figure 2B:
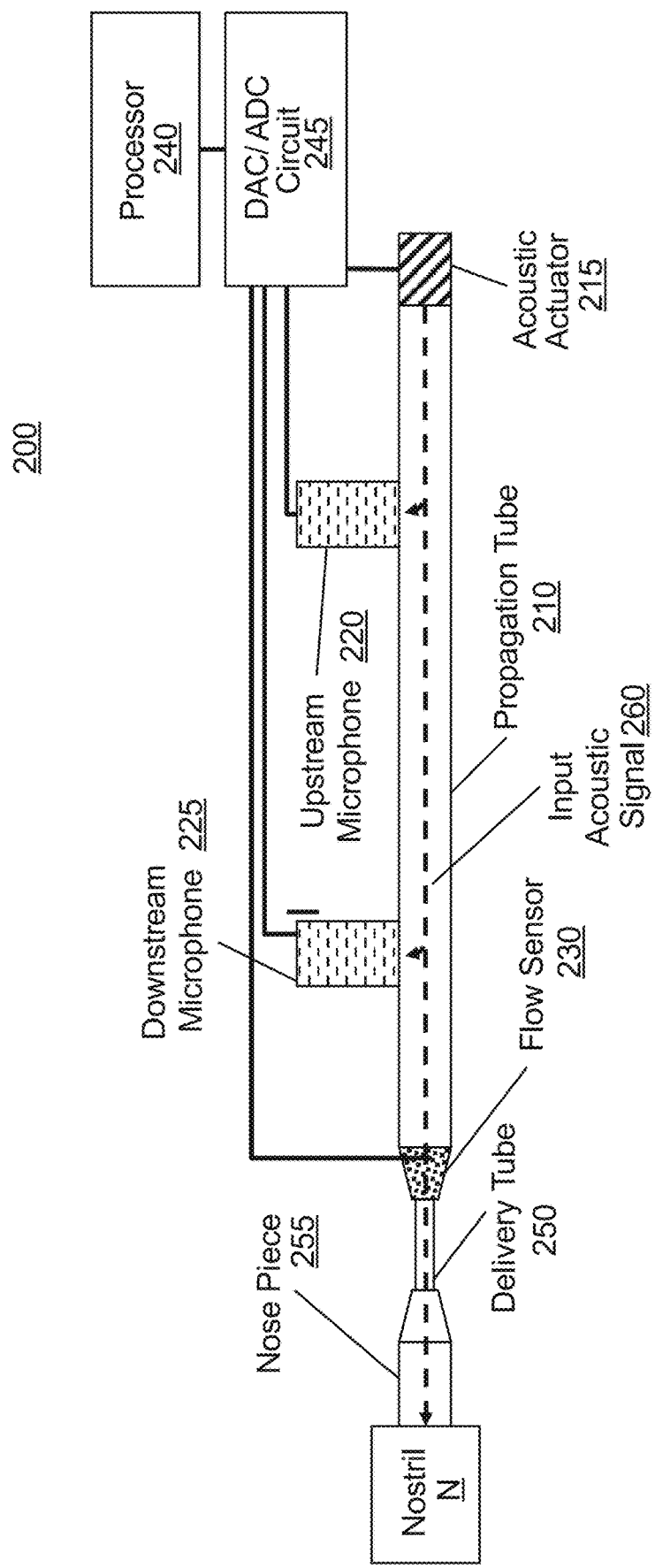
FIG. 2B illustrates the example acoustic system of FIG. 2A with an input acoustic signal applied to the nostrils of the subject.
Figure 2C:
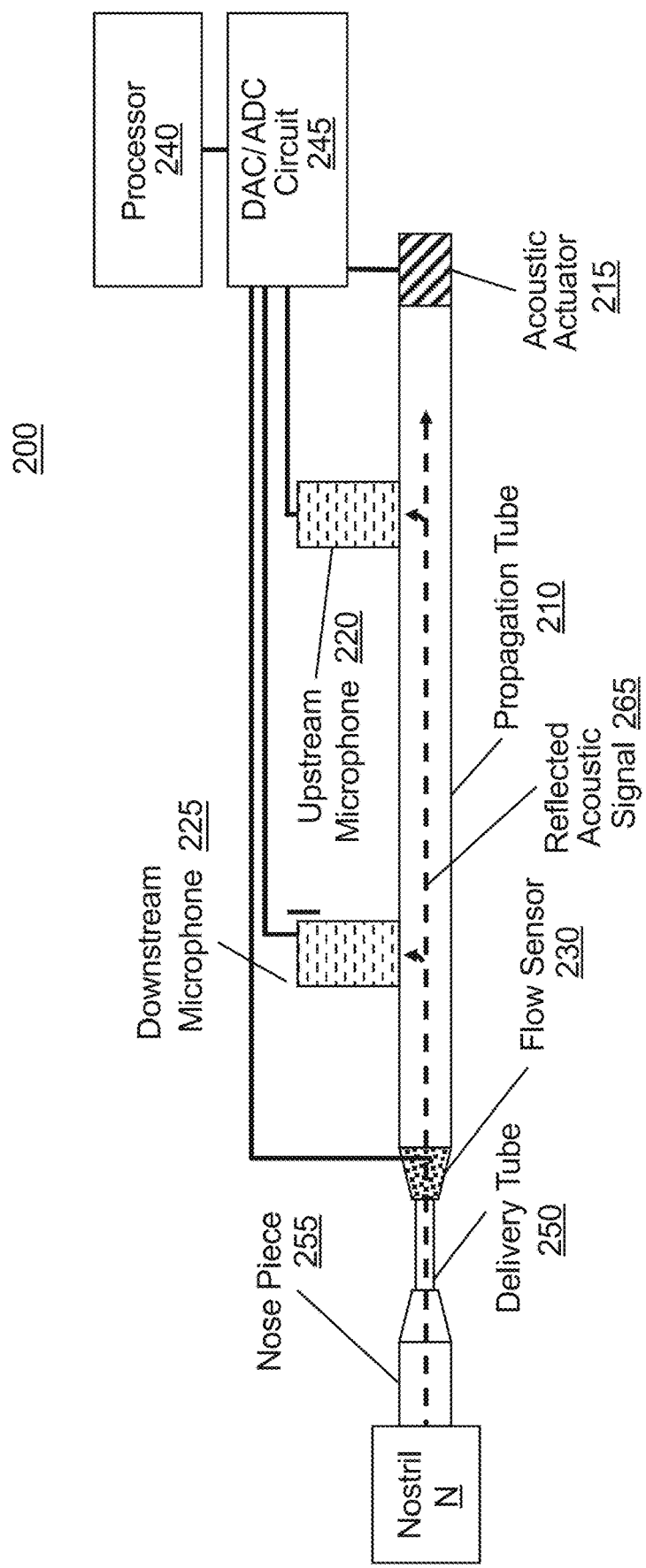
FIG. 2C illustrates the example acoustic system of FIG. 2A with a reflected acoustic signal received from the nostrils of the subject responsive to the input acoustic signal of FIG. 2B.
Figure 2D:
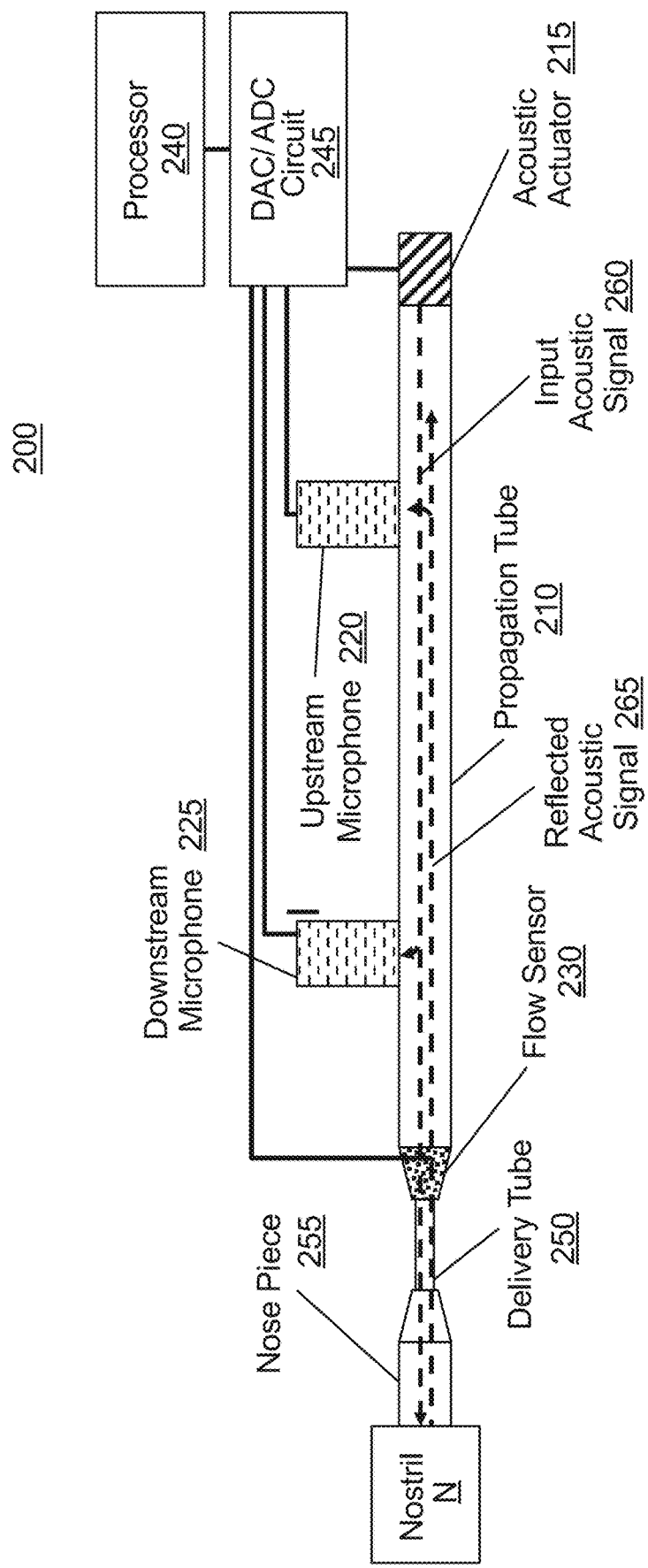
FIG. 2D illustrates the example acoustic system of FIG. 2A, and further illustrates the use of different microphones to detect the input acoustic signal of FIG. 2B and the output acoustic signal of FIG. 2C.
Figure 3:
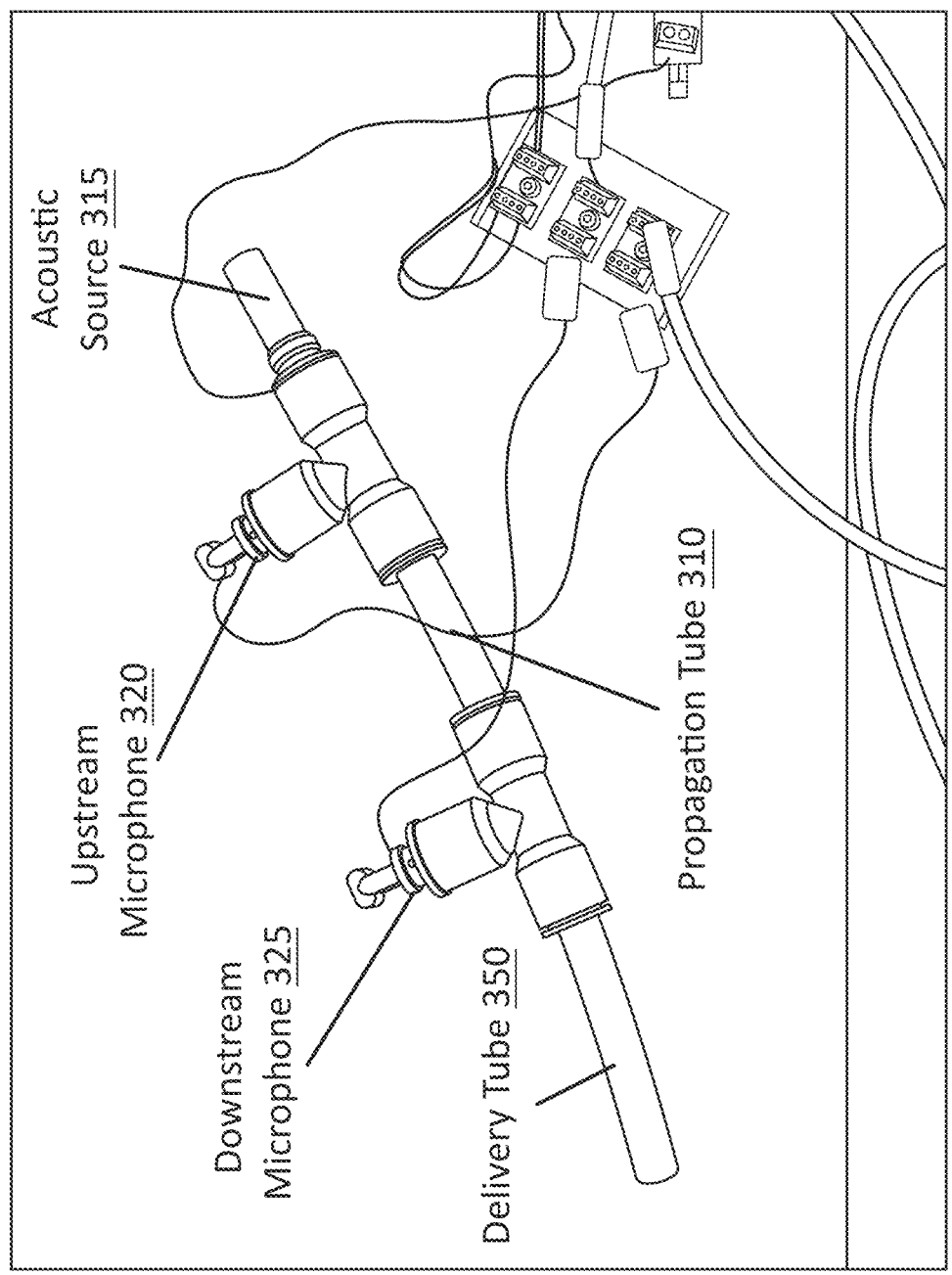
FIG. 3 is a photograph of an example acoustic system.

The system 200 also includes acoustic-sensing microphones 220, 225 (e.g., similar to the acoustic sensor of the unit 130), though any suitable acoustic transducers can be employed, such as, for example The TDK InvenSense ICS-40618 illustrated in FIG. 3, and structurally and/or functionally similar variants thereof. Generally, any microphone with acceptable sensitivity (e.g., up to 20 kHz) can be employed. The microphones 220, 225 can independently be, for example, resistive microphones, condenser microphones, fiber-optic microphones, piezoelectric microphones, electret microphones, and/or the like. As illustrated in FIGS. 2A-2D, the microphone 220, sometimes referred to as the 'upstream' microphone is distal from the nostril N compared to the microphone 225, which is sometimes referred to as the 'downstream' microphone.

In some cases, one microphone (i.e., either the microphone 220 or 225, but not both) is employed. Such a setup can provide for a simpler configuration when, for example, the acoustic actuator 215 is well characterized and produces a well defined waveform, when dynamics of the single microphone are well characterized, and/or the like. In some cases, the system 200 can include more than two microphones such as to, for example, have backup options in case one or both the microphones 220, 225 fail, to validate readings and/or operation of the microphones 220, 225, to provide a variable and selectable separation between two microphones, and/or the like.

FIG. 3 is a picture of an example system 300, which include several components illustrated and described for the system 200 of FIG. 2. Shown is an acoustic source 315 (e.g., similar to the actuator 215), an upstream microphone 320 (e.g., similar to the microphone 220), a downstream microphone 325 (e.g., similar to the microphone 225). In the system 300, a propagation tube 310 is formed between the microphones 320, 325, and a delivery tube 350 is coupled to an end of the downstream microphone 325.

Referring again to FIGS. 2A-2D, the circuit 245 also includes an analog-to-digital converter (ADC), that can receive an indication of the detected acoustic response from the microphones 220, 225, and can transmit to a microprocessor/controller for analysis. The ADC converts analog signals from the microphones 220, 225 into digital signals suitable for analysis by the processor 240. The processor 240, the circuit 245, the actuator 215, the propagation tube 210, the flow sensor 230, and the microphones 220, 225 can be enclosed in a casing similar to the casing 110.

The acoustic systems 100, 200 can generally be used as follows. Described with reference to FIGS. 1 and 2A-2D, the casing 110 can be attached to the subject/animal S (e.g., various parts could be mounted on the head, back, abdomen, and/or legs), and one or both nosepieces 255 can be inserted into the nostrils N of the animal S. The processor 240 can drive the acoustic actuator 215 with a predetermined actuation signal. An example actuation signal can be one that has a uniform power spectral density from 100 Hz to 20 kHz. The amplitude of the actuation signal can be set and/or determined experimentally to prevent subject unease and distortion in the actuator response. Duration of the actuation signal can be less than about 250 ms, around 250 ms or more than 250 ms, including all values and sub-ranges in between.

Figure 4C:
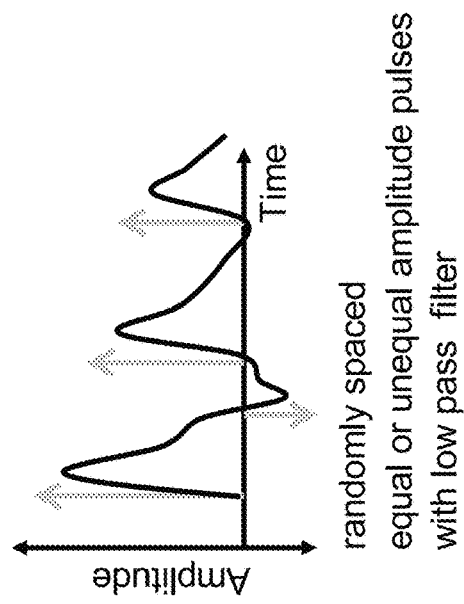
FIG. 4C is a plot of an example actuation signal of FIG. 4B after passing through a low pass filter.
Figure 4B:
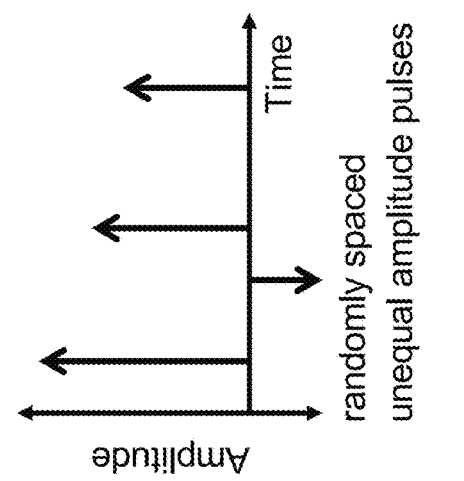
FIG. 4B is a plot of an example actuation signal having randomly spaced, unequal amplitude pulses for generating an acoustic signal in an acoustic system.
Figure 4A:
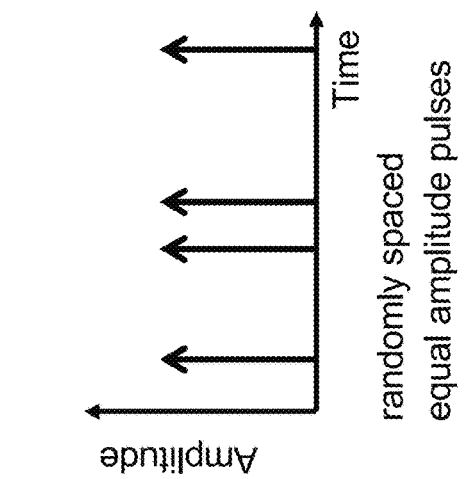
FIG. 4A is a plot of an example actuation signal having randomly spaced, equal amplitude pulses for generating an acoustic signal in an acoustic system.
Figure 4D:
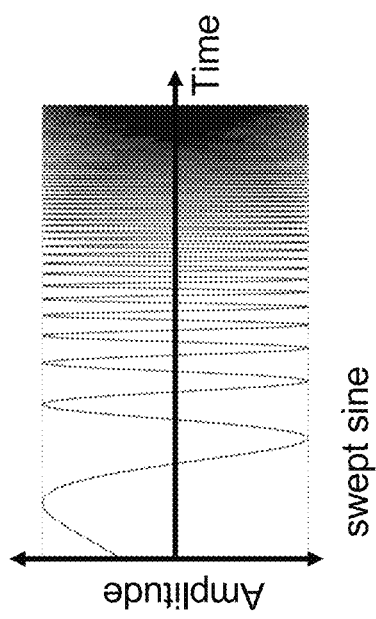
FIG. 4D is a plot of an example actuation signal that is a swept sine wave.
Figure 4E:
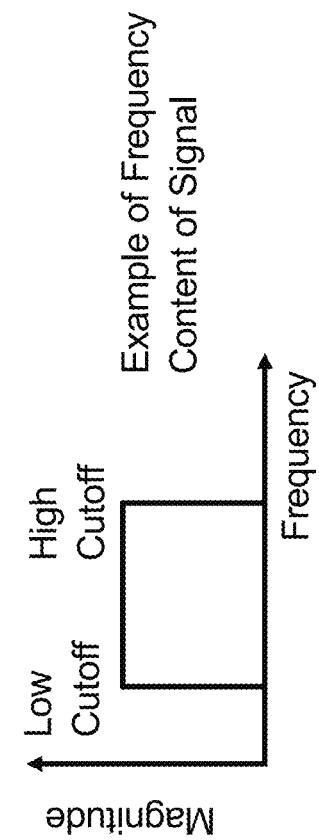
FIG. 4E is a plot illustrating frequency content of the signal of FIG. 4D.

The actuation signal can include, for example, randomly spaced and equal amplitude pulses as illustrated in FIG. 4A, or randomly spaced and unequal amplitude pulses as illustrated in FIG. 4B. FIG. 4C illustrates the actuation signal as randomly spaced pulses of equal or unequal amplitude passed through a low-pass filter, with the light arrows illustrating the pre-filtered pulses, and the dark curve illustrating the post-filter actuation signal that is applied to the actuator 215. The cutoff frequency of the low-pass filter can be set and/or selected to not exceed the maximum frequency that the actuator can produce, to increase the likelihood that the acoustic signal generated by the actuator 215 matches and/or faithfully reproduces the actuation signal. The actuation signal can also include a swept sine wave as illustrated in FIGS. 4D, 4E, or any another suitable signal. Without being limited by any theory in particular, a higher power signal that would be tolerated by the subject S may be selected and desirable. One factor in selecting such an actuation signal can be basing it on spread of the power spectral density of the actuation signal as a function of frequency, with greater spread associated with a greater likelihood that the subject can tolerate it.

The frequency/frequencies in the input acoustic signal, also sometimes referred to as a "first acoustic signal", so generated by the actuator 215 can be selected to match, to not match, to exceed, any frequencies known to resonate within the nostrils N. The frequencies can be selected to prevent resonance in the respiratory tract of the subject S, which can be distressful to the subject. FIG. 2B illustrates generation and application of an input acoustic signal 260 to the nostrils N.

As non-limiting examples, the input acoustic signal can be any acoustic signal with two or more values of amplitude for linear system identification (e.g., a binary input) of the subject S' nasal passages, or any signal with three or more values for static nonlinear system identification (e.g., a trinary input), or any signal operating at a higher number of discrete amplitude levels. The frequency of the input acoustic signal can be from 100 Hz to 20 kHz, greater than 20 kHz (e.g., up to about 100 kHz) such as when, for example the actuator 215 includes a broadband acoustic transducer. However, acoustic actuators generating acoustic signals at frequencies greater than 100 kHz can also be employed of system identification such as, for example, spark actuators and some piezoelectric actuators. Frequency selection for the input acoustic signal can be based on, for example, and particularly at higher frequencies where acoustic attenuation is higher, whether the input power required or desired to receive a reflection from the nearest geometric feature in the subject S's nasal passageways may be too high to be practical, may cause discomfort to the subject S, may render the subject S less likely to be compliant, and/or the like.

As one example, linear system identification, also sometimes referred to as linear dynamic estimation, for the systems 100, 200 can be generally carried out as detailed in PCT Publication No. WO 2020/149932, the entire disclosure of which is incorporated herein by reference. For example, an example frequency domain approach for analyzing linear, time invariant systems can involves manipulating power spectral calculations of the input and output signals as per the following steps:

1) An impulse response length N (this also specifies frequency resolution, which is (Sample Rate)/N) is specified.
2) The input and output signal (e.g., the input and reflected acoustic signals) are split into N-length input and output segments. These segments are windowed using a Hanning window and overlap by 50%.
3) An input power auto spectrum (Sxx), output power auto spectrum (Syy), and input-output power cross spectrum (Sxy) are calculated on each segment. These spectra can be calculated in the MATLAB computing environment developed by Mathworks. Syntax used to compute the individual power spectra is:

3a) Sxx=abs(fft(Input Segment)).^2 % input power auto spectrum
 3b) Syy=abs(fft(Output Segment)).^2 % output power auto spectrum
 3c) Sxy=conj(fft(Input Segment)).*fft(Output Segment); % input output power cross spectrum The standard FFT (Fast Fourier Transform) algorithm in most computer languages can handle power-2 length signals, and as a result the impulse response length N can also be of power-2 length. In other computer languages, other algorithms that can handle non-power-2 length signals, including prime factorization algorithms and the CZT (Chirp-Z Transform) algorithm, can be employed, which can loosen the restrictions on the signal length.

4) Then, the Sxx, Syy, and Sxy calculated for each N length segment can be averaged, and the following can be calculated with the mean power spectra according to the following syntax:
 4a) H=Sxymean./Sxxmean % frequency response transfer function 4b) Gain=abs(H) % transfer function gain
4c) Phase=unwrap(angle(H)) % transfer function phase
4d) MSC=abs(Sxymean.*conj(Sxymean)./(Sxxmean.*Syymean)).^2% Magnitude Squared Coherence
4e) h=ifft(H) % time domain impulse response This division of the input-output cross power spectrum by the input auto power spectrum is the frequency-domain equivalent of deconvolving the input auto-correlation function from the input-output cross-correlation function (e.g., via Toeplitz matrix inversion) in the time (or lag) domain. A frequency-domain analysis approach (requiring vectors of length N) can be made to operate within the memory constraints of a personal computer much more readily than a time-domain analysis approach (requiring arrays of size $N^2$) for large N, but both approaches are valid.

In addition to gain and phase (which are commonly shown in a Bode plot), one can also calculate and report magnitude square coherence, which can be one measure for evaluating the validity of the gain and phase estimates, to ensure that the estimates reported by a transfer function's gain and phase represent real system dynamics, and are not simply noise or nonlinear effects in the measurements. The square of the coherence function can be employed as a measure of the output variance accounted for (VAF) by the estimate at each frequency. The coherence can range from between 0 and 1. When the coherence is near 1, the system is linear and the noise in the measurement is small. When the coherence is near 0, nonlinear behavior and/or noise can be present that overpowers the measurements. While VAF typically gives a single number to represent the quantitative measure of the success of the model, the coherence squared function can be representative of the breakdown of the VAF as a function of frequency.

Figure 5D:
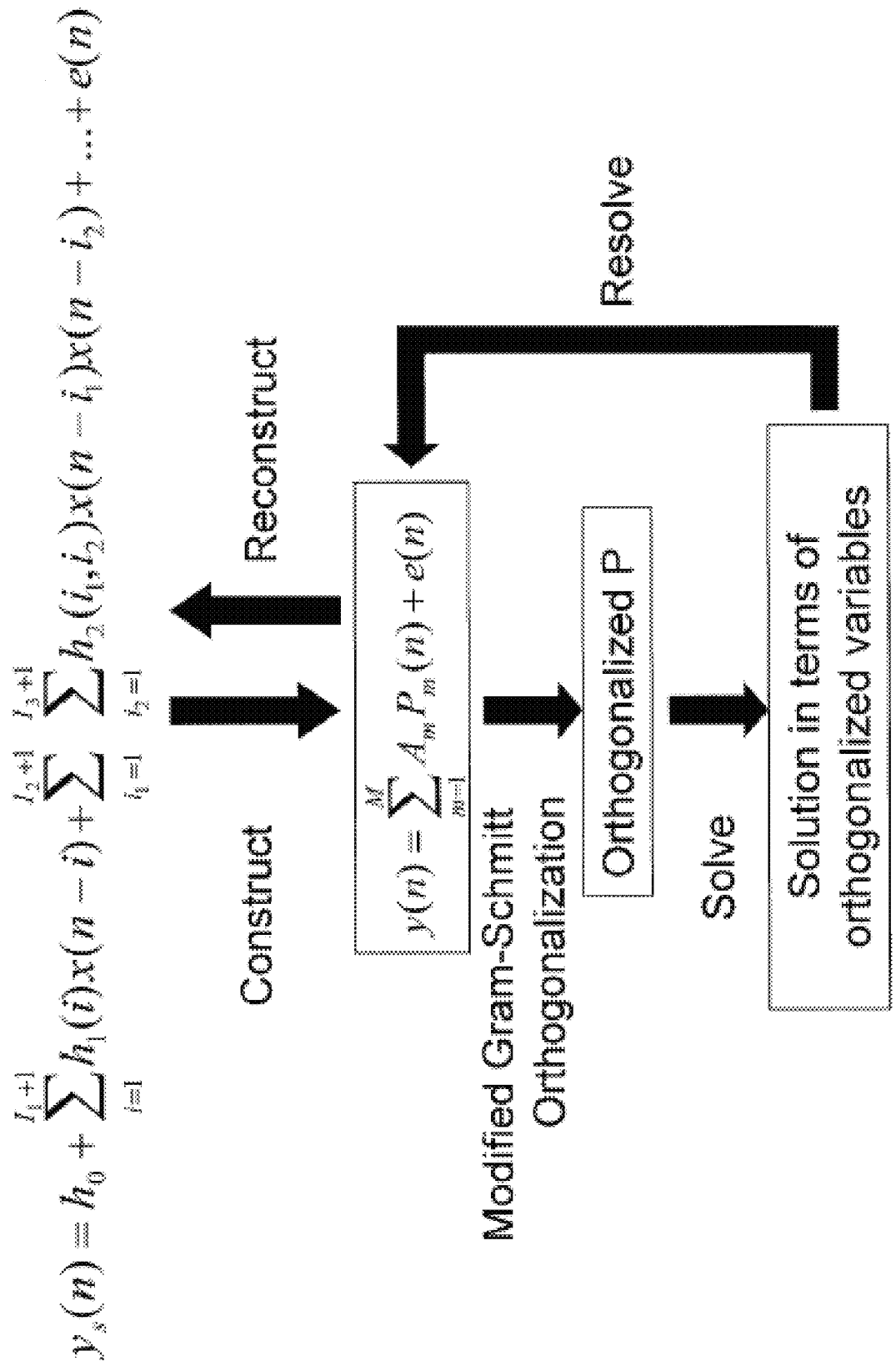
FIG. 5D illustrates an example approach to solve for Volterra kernels, including constructing the kernel, orthogonalization, solving, resolving, and reconstruction.
Figure 6:
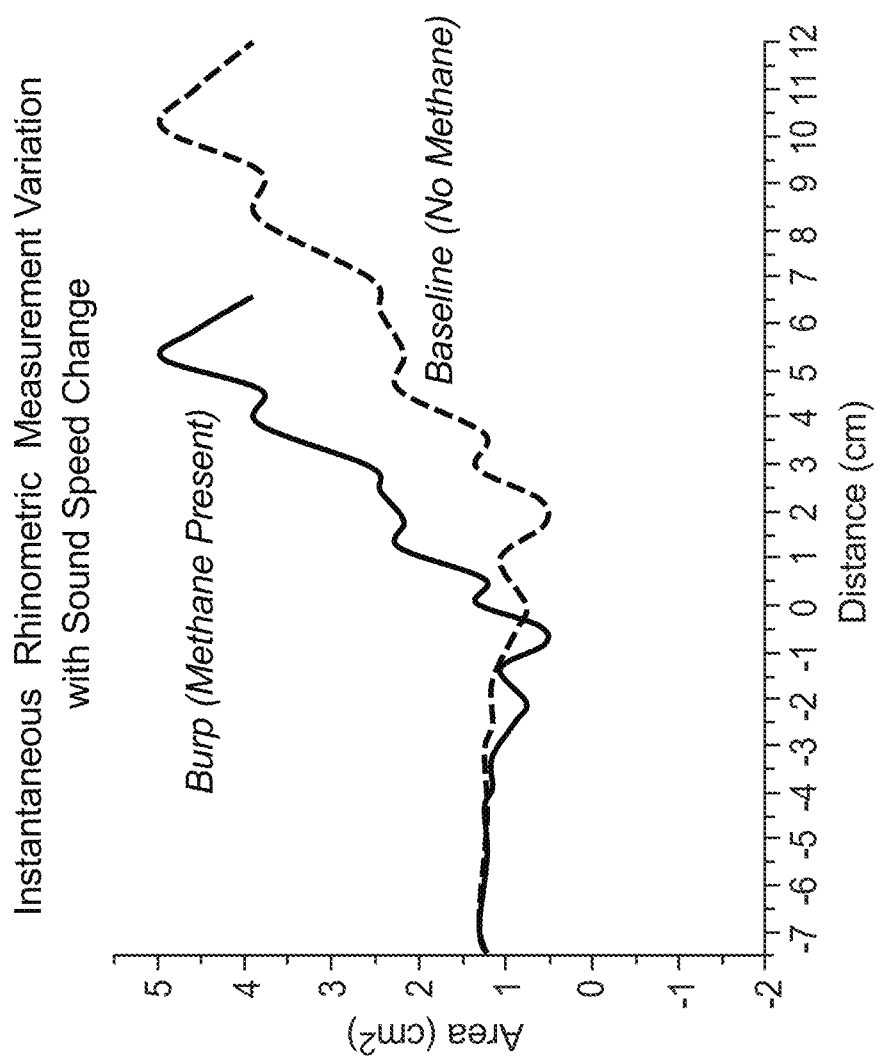
FIG. 6 is a plot illustrating burp detection in a ruminant subject animal.

As an example for when the systems 100, 200 exhibit nonlinear behavior, they can be modeled as a Wiener static nonlinear model, and the above process described for determining the linear dynamic model can be deployed initially between the input to the linear system and the output of the static nonlinearity (FIG. 5B) to produce a prediction of the linear component. This can be combined with the measured input to produce an estimate of the linear system's output. This estimate of the linear output can be plotted against the measured output from the static nonlinearity to reveal the behavior of the static nonlinearity. A nonlinear function can be fit to this plot, which will give an estimate for the static nonlinear element. When the nonlinear model (linear dynamics and static nonlinearity) is convolved with the original input of the example measurements, a predicted non-linear output can be obtained. If the resulting VAF increases from the VAF achieved using the linear model prediction, this indicates that the nonlinear model can better explain the dynamics of the system.

These estimates of the linear dynamic model and the static nonlinearity can be refined. For example, by determining the reversion of the previous estimate of the nonlinear function and applying it to the measured output of the static nonlinearity, one can determine an estimate for the output of the linear dynamic element. This can then be used as the output (and the measured input to the linear dynamic element can be used as the input) for the linear system identification process described previously. This can produce an updated estimate of the linear dynamics, which can again be convolved with the measured input and plotted against the measured output of the static nonlinearity to allow for the nonlinear function to be updated. This process can be iteratively repeated until the linear dynamic model and the static nonlinearity have converged.

As another example, a similar iterative process to that described above for the Wiener Static Nonlinear Model Estimation can be undertaken to determine the static nonlinear dynamics and the linear dynamics for a Hammerstein static nonlinear model (FIG. 5C), albeit working from the opposite direction. One can start with the measured output of the linear dynamic system, which when combined with an estimate of the linear dynamics, can be used to estimate the input to the linear dynamic system. This estimate can be plotted against the input to the static nonlinearity that precedes the linear dynamic element to fit a nonlinear function that estimates the behavior of the static nonlinearity. The estimates for the linear and nonlinear behavior can be iterated upon for the Hammerstein Static Nonlinear model estimation in an analogical manner to the iterative process described for refining the Wiener model's dynamic linear and static nonlinear components.

As yet another example, instead of using iterative techniques to identify static nonlinearities such as Wiener and Hammerstein nonlinearities described above, a technique for determining the Volterra kernels can be used as generally disclosed in U.S. Pat. No. 8,758,271, the entire disclosure of which is incorporated herein by reference. Generally, the Volterra series is a functional expansion of the general time-invariant nonlinear dynamic system problem. The idea behind the functional expansion is that the zero-th order kernel represents the system average. The first order kernel represents the first order linear perturbation to the system where the output depends linearly on lagged inputs. This kernel is exactly the linear impulse response function. The second order kernel represents the second order perturbation to the system where the "impulse response" function is not a function of one lag but a function of two lags. This means that the input at some time can interact with the input at another time to produce an effect on the output, This concept can be expanded to higher orders. For a system with a finite memory length I, the discrete functional expansion can be written as:

$$y_\Delta(n) = \qquad (1)$$
$$h_0 + \sum_{i=1}^{I_1+1} h_1(i)x(n-i) + \sum_{i_1=1}^{I_2+1}\sum_{i_2=1}^{I_3+I} h_2(i_1, i_2)x(n-i_1)x(n-i_2) + \ldots + e(n)$$

Equation 1 allows for memory lengths $I_1$, $I_2$, $I_3$, etc., to be different for different kernels. Memory lengths $I_1$, $I_2$, $I_3$, etc., can be the same and may be equal to memory length I. The Volterra expansion can be difficult to solve, since the expansion contains many parameters in $h_1$, $h_2$, etc. which grow very quickly with the memory length and kernel order. Additionally, the system is not orthogonal so changing one value will change the optimal fit for other values in the series.

The Volterra kernel is, however, one functional expansion among many for nonlinear dynamic systems. A modification to the Volterra kernel can make solving the systems 100, 200 much simpler. The Wiener functional expansion orthogonalizes the Volterra series for an assumed form on the input. By using assumptions for Gaussian white inputs, one can create a different expansion such that the first kernel can be solved independent of the second kernel. This means that any noise remaining after solving the first order kernel must either be noise or components of higher order kernels. The Wiener and Volterra kernel solutions may not be exactly the same. The zeroth order Wiener kernels are the mean output for one type of Gaussian white input, The first and second kernels, however, are the same for the two systems as long as there are no higher order kernels.

Several Wiener kernel solution techniques exist including cross-correlation methods, repeated Toeplitz matrix inversion techniques, and use of functional expansions. One consideration of the Wiener functional expansion is that only white inputs can be used. Since real inputs can only become white asymptotically, there can be some inherent uncertainty in the solutions for short test lengths. In addition, the input to a real system is rarely optimally Gaussian and white. It is possible to create orthogonal expansions for different types of inputs, however not every mathematical function has properties that would allow this to be readily accomplished. In addition, it may become cumbersome to do system identification if a new expansion needs to be derived for every new input.

There are several different methods that can be used to solve Volterra kernels. One such method imposes no constraint on the input type (i.e., input does not need to be Gaussian and white to be solved), length, or smoothing constraints used on the kernels. Because of the benefits of this method, it can be used as the basis for techniques described herein for obtaining results. Because this method requires a few modifications for the input types used in this work, additional implications and methods for obtaining interpretable kernel data are described below.

Specifically, this method can encompass an exact orthonormalization step for the input, a solution step in the orthonormalized space, and a reconstruction step to take the solution back into the space of the Volterra kernel. A summary of the solution steps are shown below and illustrated in FIG. 5D:

1. Construct: Sort the input data according to a set of rules.
2. Orthonormalization: Use a modified Gram-Schmidt solver to orthonormalize the input data.
3. Solve: obtain an orthonormalized solution.
4. Resolve: use the inverse of the Gram-Schmidt process to put the solution back into its original terms.
5. Reconstruct: use the same partitioning rules to resolve the kernel responses.

Gram-Schmidt orthogonalization is the same as that used to orthogonalize the Wiener kernels. Steps 1 and 5 can be are dependent on different partitioning rules, which satisfy constraints from the modified Gram-Schmidt orthonormalization process. The terms orthonormalization and orthogonalization are used interchangeably here.

Many physically realizable, finite memory systems can be modeled from an input output relation that is shown, $$y(n) = \sum_{m=1}^{M} A_m P_m(n) + e(n). \tag{2}$$

In the simplest linear case, y(n) is the output of the single input single output system, $A_m$ is the impulse response of the system with memory M and $P_m(n)$ (which is not position in this case) is simply equal to the input $x(n-m-1)$. The measurement contains some error e(n). From this form, one can obtain a linear input output relation. In the more general case, m is a value, which stores the dynamic memory of the system, which stores input lag information while n represents the value at a given time. The $P_m(n)$, however stores information for a particular set of rules that apply at a given m and n. This implies that $A_m$ is a series that is convolved with $P_m(n)$ to produce the desired output where $P_m(n)$ is constructed based on some partitioning rule. It can be difficult to directly solve this equation (2), and therefore it may be desirable that it be orthonormalized into a different form in terms of variables $\gamma_m$ and $\beta_m$, as illustrated in equation (3) below.

$$y(n) = \sum_{m=1}^{M} \gamma_m \beta_m(n) + e(n). \tag{3}$$

Generally, the processor 240 can perform system identification of the Subject S's nasal passages by accounting for, receiving as input, or otherwise employing, knowledge of the actual acoustic input signal generated by the actuator 215 and of the reflected acoustic output signal(s) sensed by the microphones 220, 225. The transfer function (or nonlinear equivalent to a transfer function) of the acoustic actuator 215 can alter characteristics (e.g., the shape, delay, frequency content, and/or the like) of the acoustic input signal relative to the actuation signal. Such differences can arise due to, for example, amplification distortion (of the actuation signal generated by the processor 240) prior to applying the actuation signal to the acoustic actuator 215, distortion due to digital-to-analog conversion of the actuation signal by the circuit 245, dispersion and/or attenuation of the acoustic signal, thermal effects, humidity effects, and/or the like.

The processor 240 can employ any combination of several approaches to compensate for these dynamics such that any differences between the expected (to be generated by the acoustic actuator 215) acoustic input signal and the actual acoustic signal can be accounted for. For example, the processor can use prior knowledge of the transfer function of the acoustic actuator 215, such as by detecting the actual acoustic input signal from the actuator 215 at the downstream microphone 225 as illustrated in FIG. 2B. As another example, the actual acoustic input signal can be estimated or detected by detecting the output of the actuator 215 at the upstream microphone 220 (as also illustrated in FIG. 2B, and employing the downstream microphone 225 to detect the actual acoustic output signal (see FIG. 2C). While both the upstream and downstream microphones 220, 225 can register the reflected acoustic waves from the nostrils N as the actual acoustic output signal, the physical distance between the microphones (e.g., from about 1 mm to about 1000 mm, including all values and sub-ranges in between) can result in a temporal difference in when these reflections are measured. This can allow for the microphones 220, 225 to be used for proxy measurements, with one being employed to measure the actual input acoustic signal and the other being employed to measure the reflected acoustic signal. An example of such an approach is illustrated in FIG. 2D, where the downstream microphone 225 is employed to measure/detect the input acoustic signal 260, and the upstream microphone 220 is employed to measure/detect the input acoustic signal 265. More generally, the input acoustic signal can be detected at the upstream microphone 220 first, and the downstream microphone 225 second. Similarly, the reflected acoustic signal can be detected at the downstream microphone 225 first and upstream microphone 220 second. So the temporal separation between the detection of these signals can be used to determine their origin. Computing the impulse response can then include using the detected signal at one microphone as the "input" to the system identification approach employed, and the other microphone as the "output".

The processor 240 can then calculate a cross-correlation function from these signals and, in the case of linear system identification of the subject S's nasal massages using a time domain approach, deconvolve the input auto-correlation function (i.e., the correlation of the input acoustic signal with a delayed version of itself) from this cross-correlation function to determine an impulse response of the subject. Generally, the impulse response can be characterized as a response of the subject to a brief input impulse, and here can be a response based on the geometry of the nasal passageways of the subject, of the composition of the gaseous mixture in the nasal passageways of the subject, and/or the like. The processor 240 can perform an equivalent analysis in the frequency domain to determine the frequency response, as the frequency response of a linear system is a Fourier Transform of its impulse response. Analogical approaches are appropriate for nonlinear system identification as described above for (for example Weiner, Hammerstein, and Volterra/Weiner Kernels.

Upon delivering the input acoustic signal to the nostrils N, a reflected acoustic signal (also referred to as a "second acoustic signal") is generated, which can travel back to the propagation tube 210 via the nose piece 255 and the delivery tube 250. The reflected acoustic signal can account for, for example, reflection, scattering, absorption, attenuation, etc. of the input acoustic signal by the tissues of the respiratory tract of the subject C, of the gas itself, and further account for both thermo-viscous losses for all gases and quantum-mechanical losses for polyatomic gases. The reflected acoustic signal can also sometimes account for whether the subject's mouth is open or closed. Without being limited by any theory in particular, every time there is a change in acoustic impedance of a cavity, the cavity wall(s) can reflect some sound and allow some sound to pass. This can happen substantially simultaneously along a cavity with a variable (e.g., continuously changing) cross section, such as the nostrils N and/or other nasal passages of the subject S. As such, any reflected acoustic signal can temporally overlap with the input acoustic signal. Accordingly, the upstream and/or downstream microphones 220, 225 can detect a combination (e.g., a superposition) of the input acoustic signal as well as the reflected acoustic signal, which is then communicated to the processor 240.

Since the input acoustic signal has been characterized as described earlier, the microprocessor can use this characterization to separate and/or otherwise isolate the reflected acoustic signal from the signal detected by the microphone(s) (sometimes also referred to as the "third acoustic signal"), using system identification as described herein. The impulse response h(t) can then be determined based on the reflected acoustic signal using any suitable linear identification technique, in the time domain or the frequency domain (see FIG. 5A). In some cases, non-linear identification techniques can be employed to model the dynamics of the acoustics of the nostrils N. Such techniques can include, for example, Wiener static nonlinear models (see FIG. 5B), Hammerstein static nonlinear models (see FIG. 5C), Volterra kernels (see FIG. 5D), Weiner kernels, NARMAX models, or parallel cascade models.

The processor 240 can them compare the measured impulse response against a baseline impulse response to determine the sound speed in the Subject S's nasal passageways. For example, and without being limited by any theory in particular, if h(t) represents the measured impulse response (e.g., where the effect of a methane-inducing burp may or may not be present) and g(t) represents the baseline impulse response (where there is no effect of a burp), a distance multiplier "m" and baseline offset "b" can be determined by the processor 240 such that the least squares error (or another error minimization approach can be employed) of h(m*t+b) with respect to g(t) is minimized. These parameters, "m" and "b", representing a temporal scaling factor and delay, respectively, can be compared by the processor 240 with a standard measure to determine the sound speed in the nasal passages (e.g., nostrils N) of the subject S. The temporal scaling factor "m" can be linearly correlated with sound speed, which can be fit and used by the processor 240 for predicting and/or estimating the sound speed in the nostrils N. An elevated sound speed compared to baseline can be indicative of the presence of methane, and the value/magnitude of the sound speed can be correlated with instantaneous methane concentration. The processor 240 can perform this correlation as a function of distance and cross-sectional area as accounted for in the measured impulse response, where the assumption of some speed of sound has already been made and it is corrected based on such parameters.

The measured baseline impulse response can be, for example, an average of several measured impulse responses (say over 5 minutes, sampled every 30 seconds) when the animal is not burping. In some cases, the processor 240 can employ detection of a sound generated by the animal (e.g., via a separate acoustic sensor) to determine when the animal is burping (and to select impulse responses for baseline averaging). For example, for establishing a baseline, the timing of sounds associated with burping can excluded from impulse response selection, since at all other (unexcluded) times the animal is likely just carrying out inhalation or exhalation.

The processor 240 can estimate the sound speed by compensating for factors such as, but not limited to, flow speed, temperature, humidity, oxygen uptake, carbon dioxide release, and/or the like. For example, a thermal probe in the apparatus can measure the temperature or indicate (e.g., when a cow is exhaling) that the temperature of the exhalation is similar to the average temperature of a healthy animal, since mammals typically thermoregulate within a narrow range. Since an ideal gas' sound speed scales with the square root of the temperature, this effect on sound speed, which otherwise may register an erroneous change in methane concentration, can be accounted for. Similar approaches may be used for the other factor listed above.

Sound speed can then be estimated as illustrated in Equation (4):

$$a_{mix} = \sqrt{\frac{\gamma_{mix} RT}{M_{mix}}} \tag{4}$$

Where $a_{mix}$ is the sound speed of a gas mixture, $\gamma_{mix}$ is the ratio of specific heats of the same gas mixture, R is the ideal gas constant, T is the temperature, and $M_{mix}$ is the molar mass of the mixture.

The processor 240 can also perform acoustic attenuation measurement as detailed in PCT Publication No. WO 2020/149932, which discusses an appropriate transmission length (e.g., around 1 m) for sensing a particular gas and is incorporated herein by reference in its entirety. Generally, an optimal transmission length that is optimal for sensing a lightly attenuating gas may be quite long (e.g., 1 meter or more), and relatively longer than for a highly attenuating gas. Here, in the case of methane measurement in an animal's nostrils, the transmission length can be specified as the distance between the upstream and downstream microphones 220, 225. Alternatively, the transmission length can be specified as twice that between one of the microphones 220, 225 at one end, and within the nasal passageway of the subject S at the other end.

The processor 240 can further calculate a volumetric methane emission rate based on the estimated methane concentration and based on a flow speed as measured by the flow sensor 230, as the subject S exhales.

While illustrated and frequently explained herein with respect to estimating sound speed in the nasal passageways of cattle, the systems 100, 200, 300 of FIGS. 1-3 can be useful for estimating sound speed in any passageway where the geometry is substantially fixed over time. Further, the systems 100, 200, 300 can be used for continuous monitoring, i.e., the nasal passageway of the subject can be repeatedly stimulated with an input audio signal, and the response repeatedly measured. This can be carried out for a predetermined number of times, a predetermined duration of time, indeterminately until (for example) a control signal is received at the processor 240 to terminate and/or pause the monitoring, and/or the like.

Discussion

Generally, the acoustic apparatuses/systems disclosed here can track methane emissions by exploiting the nostril-accessible nasal pathway of an animal, and more generally can include an apparatus associated with a volume that receives a material (such as gas), where the volume has one or more features that reflect acoustic energy. The apparatus can include an acoustic actuator coupled to an animal's airway to perturb the animal's airway with an acoustic signal, and a controller to measure acoustic signals in response. Analysis of the measured signals can yield a response to the perturbation, where the response to the perturbation is a function of the material contained in the volume and the geometry of the volume. A change in the material (makeup, temperature, pressure, etc.) causes a change in the response, and this changed response can be compared to the original response. The material can be a fluid or a solid. Each response can be indicative the speed of sound, and can be compared to a previously measured response to determine a change, if any. The volume can be part of an inanimate object (like a piece of tubing where pinching needs to be detected), a nostril in an animal, the mouth and/or trachea of an animal, the ear of an animal, and/or the like. The feature(s) that reflect acoustic energy can do so by causing a change in the volume's acoustic impedance.

Actuators and microphones used in the apparatus can be similar to those currently found in cell phones, which in turn can make the acoustic apparatus small, portable, and rugged enough for extended outdoor use. The nostril geometry can be mapped using sound waves, similar to the mapping done by an acoustic rhinometer. However, where acoustic rhinometers assume a constant speed of sound to measure changes in geometry, an acoustic apparatus as disclosed herein can assume constant geometry to measure changes in the speed of sound. Said another way, approaches disclosed herein can exploit the notion of using the fixed geometry of a given volume to measure these changes. When the volume is fixed, the change in the response can be a proxy for the change in the speed of sound in the volume due to, for example, a fluid disposed in the volume. Without being limited by theory, the speed of sound in methane is higher than in any other gas typically found in a cow's nostril, i.e., higher than nitrogen, oxygen, carbon dioxide, and water vapor. Accordingly, the acoustic apparatus/systems disclosed here are useful with any gas, such as (for example) methane, hydrogen, helium, etc. that has a speed of sound higher than the other gases mentioned above. In some cases, the acoustic apparatus/systems disclosed here are useful with any gas that has a speed of sound lower than the other gases mentioned above, and when the speed of other common gases like oxygen and carbon dioxide, both of which also have relatively lower speeds than those mentioned above, are accounted for.

Conventional acoustic rhinometers rely on analyzing reflected clicks with rudimentary delay calculations. In contrast, the acoustic apparatuses/systems described here can perturb the animal's airway with a stochastic (e.g., non naturally occurring) input signal to elicit the characteristic response quickly (due to relatively higher power delivery obtainable with a stochastic signal vs. sporadic impulses) and with better fidelity due to the higher power/energy delivery. Low cost acoustic transducers and system identification techniques can be employed to detect and analyze the results. The apparatus can acquire a baseline measurement for each particular animal and compare subsequent measurements against this baseline to detect and quantify methane emissions.

Aspects disclosed herein can also encompass acoustic rhinometers (where speed of sound is known or assumed, and geometry changes are of interest) that use stochastic system identification. The system analysis can include determining a linear dynamic component to model the characteristic response of the subject's nasal passages, determining a non-linear static component to model the characteristic response, using a first Volterra kernel and at least one higher-order Volterra kernel to model the characteristic response, determining at least one of a parallel cascade, a NARMAX (Nonlinear AutoRegressive Moving Average with eXogenous input) representation, a Wiener kernel, and/or the like.

Applications

The materials cost for such acoustic systems can be less than $20 when produced at scale. Example users of such apparatuses and systems can include farmers, environmental non-governmental organizations (NGOs), governmental regulators, and/or any group that desires decreasing methane emissions (e.g., to combat climate change) or increasing methane emissions (e.g., to generate fuel for capture).

Another example application for such sound speed measurement can be in industrial gas vents or chimneys that irregularly "belch" gases with known compositions different from that of the air, which result in differences in sound speed. A "nostril" could be constructed on the vent which does not impede the flow but provides a known acoustically reflective geometry, and used for monitoring emission events and emission volume.

Another example application can be for determining when gas-supply tubing (e.g., polymer tubing) is partially or fully kinked. One example is the monitoring of patients that use supplemental oxygen. Flow rates can be quite small, making many traditional flow measurement techniques not applicable. An acoustic apparatus/system as disclosed herein could provide kink monitoring detection by monitoring when a change in cross-sectional area occurs, which in turn would result in a change in the acoustic reflective response of the tubing.

Additionally, aspects disclosed herein can be directed to increasing methane production for commercial uses by capturing the gas emitted by cattle, and can be useful for farmers, energy companies, etc. Methane is a potent fuel and the main component of natural gas. If all methane produced by cattle globally can be collected, it could satisfy 10% of humanity's global natural gas consumption. Thus, cattle can be employed as methane-producing bioreactors.

Conclusion

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method of estimating a concentration of methane emissions from a ruminant animal, the method comprising: coupling an acoustic actuator to a nasal passageway of the ruminant animal; applying an actuation signal to the acoustic actuator to generate and deliver a first acoustic signal into the nasal passageway, such that the nasal passageway reflects the first acoustic signal as a second acoustic signal;
    collectively detecting the first acoustic signal and the second acoustic signal;
    isolating the second acoustic signal from the collectively detected first and second acoustic signals;
    estimating a sound speed through the nasal passageway based on the second acoustic signal; and estimating methane concentration in the nasal passageway based on the estimated sound speed.

2. The method of claim 1, wherein the actuation signal includes randomly spaced pulses having unequal amplitudes.

3. The method of claim 1, wherein the steps of said coupling, applying, detecting, isolating, estimating the sound speed, and estimating the methane concentration are repeated continuously.

4. The method of claim 1, further comprising:
determining a measured impulse response of the nasal passageway based on the isolated second acoustic signal, and
wherein estimating the sound speed includes comparing the measured impulse response against a baseline impulse response of the nasal passageway, the baseline impulse response associated with an absence of methane in the nasal passageway.

5. The method of claim 4, further comprising, prior to applying the actuation signal:
determining the baseline impulse response of the ruminant animal.

6. The method of claim 1, wherein estimating the methane concentration includes compensating for at least one of flow speed, temperature, humidity, oxygen uptake, or carbon dioxide release.

7. The method of claim 1, further comprising:
detecting a flow speed of exhalation from the nasal passageway by the ruminant animal; and
estimating, based on the estimated methane concentration and the flow speed, a volumetric methane emission rate for the ruminant animal.

8. The method of claim 1, wherein estimating the sound speed further comprises:
generating, via system identification and based on the detected first acoustic signal and the second acoustic signal, a model of the nasal passageway of the ruminant animal;
determining a measured impulse response of the nasal passageway based on the model; and
estimating the sound speed by comparing the measured impulse response against a baseline impulse response of the nasal passageway, the baseline impulse response associated with an absence of methane in the nasal passageway of the ruminant animal.

9. The method of claim 8, wherein the system identification is non-linear system identification, and wherein the model is selected from the group consisting of a Wiener static nonlinear model, a Hammerstein static nonlinear model, a Volterra kernel, a Weiner kernel, a NARMAX model, and a parallel cascade model.

10. A system for measurement of methane emissions, the system comprising: an acoustic actuator to generate a first acoustic signal; a propagation tube, having a proximal end in acoustic communication with the acoustic actuator, to guide the first acoustic signal to a distal end of the propagation tube; a delivery tube, coupled to the distal end of the propagation tube, to deliver the first acoustic signal to a nasal passageway of a ruminant animal and to receive a second acoustic signal reflected by the nasal passageway; a first microphone, in acoustic communication with a first point on the propagation tube, to detect at least one of the first acoustic signal or the second acoustic signal; a second microphone, in acoustic communication with a second point on the propagation tube between the first point and the distal end of the propagation tube, to collectively detect the first acoustic signal and the second acoustic signal; and a processor, operably coupled to the first microphone and the second microphone, to:
isolate the second acoustic signal from the collectively detected first and second acoustic signals; estimate a sound speed associated with the nasal passageway based on the second acoustic signal; and
estimate methane concentration in the nasal passageway based on the estimated sound speed.

11. The system of claim 10, further comprising:
a casing containing the acoustic actuator, the propagation tube, the first microphone, the second microphone, and the processor; and
a harness to removably attach the casing to the head of the ruminant animal during use.

12. The system of claim 10, further comprising:
a flow sensor, operably coupled to the processor, to detect a flow speed of exhalation from the nasal passageway by the ruminant animal, and
wherein the processor is further configured to estimate, based on the estimated methane concentration and the flow speed, a volumetric methane emission rate of the ruminant animal.

13. The system of claim 10, wherein the processor is further configured to determine a measured impulse response based on the second acoustic signal and to compare the measured impulse response against a baseline impulse response associated with an absence of methane in the nasal passageway to estimate the sound speed.

14. The system of claim 10, wherein a spacing between the first microphone and the second microphone is from about 1 mm to about 1000 mm.

15. A method of estimating a concentration of methane emissions from a ruminant animal, the method comprising:
coupling an acoustic actuator to a nasal passageway of the ruminant animal;
applying an actuation signal to the acoustic actuator to generate and deliver a first acoustic signal into the nasal passageway, such that the nasal passageway reflects the first acoustic signal as a second acoustic signal;
determining an impulse response of the nasal passageway based on the second acoustic signal;
estimating a sound speed associated with the nasal passageway based on the impulse response, based on a baseline impulse response of the nasal passageway, the baseline impulse response associated with an absence of methane in the nasal passageway, the baseline impulse response based on an assumption of fixed geometry of the nasal passageway; and
estimating a methane concentration in the nasal passageway based on the sound speed.

16. The method of claim 15, wherein determining the impulse response further comprises:
generating, via system identification and based on the first acoustic signal and the second acoustic signal, a model of the nasal passageway of the ruminant animal; and
determining the impulse response based on the model.

17. The method of claim 16, wherein the system identification is non-linear system identification, and wherein the model is selected from the group consisting of a Wiener static nonlinear model, a Hammerstein static nonlinear model, a Volterra kernel, a Weiner kernel, a NARMAX model, and a parallel cascade model.

18. The method of claim 15, wherein the actuation signal includes randomly spaced pulses having unequal amplitudes.

19. The method of claim 15, further comprising, prior to applying the actuation signal:
   determining the baseline impulse response of the ruminant animal.

20. The method of claim 15, wherein estimating the methane concentration includes compensating for at least one of flow speed, temperature, humidity, oxygen uptake, or carbon dioxide release.

\* \* \* \* \*